United States Patent [19]

Yamaguchi et al.

[11] Patent Number: 4,885,023
[45] Date of Patent: * Dec. 5, 1989

[54] THIADIAZABICYCLONONANE DERIVATIVES AND HERBICIDAL COMPOSITIONS

[75] Inventors: Mikio Yamaguchi; Yukihiro Watase, both of Shizuoka; Takeshi Kambe, Tokyo; Susumu Katou, Shizuoka, all of Japan

[73] Assignees: Kumiai Chemical Industry Co., Ltd.; Ihara Chemical Industry Co., Ltd., both of Tokyo, Japan

[*] Notice: The portion of the term of this patent subsequent to Mar. 28, 2006 has been disclaimed.

[21] Appl. No.: 136,763

[22] Filed: Dec. 22, 1987

[30] Foreign Application Priority Data

Dec. 24, 1986 [JP] Japan .................................. 61-310423
Sep. 26, 1987 [JP] Japan .................................. 62-242300

[51] Int. Cl.$^4$ .................... C07D 513/04; A01N 43/82
[52] U.S. Cl. ........................................ 71/90; 544/235; 544/224
[58] Field of Search ............................ 544/235; 71/90

[56] References Cited

U.S. PATENT DOCUMENTS 4,816,063 3/1989 Yamaguchi et al. .................... 71/90

FOREIGN PATENT DOCUMENTS 62-91 1/1987 Japan .

OTHER PUBLICATIONS

Mojé et al., *J. Org. Chem.*, vol. 39 p. 2951 (1974).
Yamaguchi et al., Chemical Abstracts, vol. 107, No. 134316 (1987).

*Primary Examiner*—Mukund J. Shah
*Assistant Examiner*—F. Bernhardt
*Attorney, Agent, or Firm*—Oblon, Spivak, McClelland, Maier & Neustadt

[57] ABSTRACT

As a herbicide, a 9-phenylimino-8-thia-1,6-diazabicyclo [4.3.0]nonane-7-one derivative having the formula:

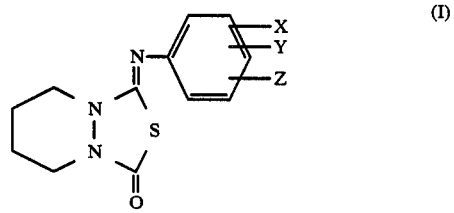

wherein each of X and Y is hydrogen or halogen, and Z is

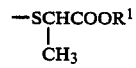

wherein $R^1$ is alkyl or cycloalkyl, or —COOR$^2$ wherein $R^2$ is alkyl.

21 Claims, No Drawings

THIADIAZABICYCLONONANE DERIVATIVES AND HERBICIDAL COMPOSITIONS

BACKGROUND OF THE INVENTION

1. Field of the Invention

The present invention relates to 9-phenylimino-8-thia-1,6-diazabicyclo-[4.3.0]nonane-7-one derivatives useful as herbicides and herbicidal compositions containing them.

2. Discussion of Background

In recent years, a number of herbicides have been developed and actually used, and they have contributed to the reduction of the agricultural work load and to the improvement of the productivity. As a herbicide having a hetero ring, oxadiazon [i.e. 5-t-butyl-3-(2,4-dichloro-5-isopropoxyphenyl)-1,3,4-oxadiazoline-2-one] is widely used. However, oxadiazon is likely to bring about phytotoxicity, when used in paddy fields, and it is not effective against perennial weeds, particularly against *Sagittaria pygmaea*. When used in upland fields, it is not so safe against crop plants such as corn or soybean and has drawbacks that its herbicidal activities are low against hardly controllable weeds such as cocklebur or morning-glory and against pigweed and lambsquaters. Accordingly, a development of a herbicide having improved herbicidal activities and safety has been desired.

SUMMARY OF THE INVENTION

Under the circumstances, the present inventors have conducted extensive researches with an aim to develop a herbicide which satisfies the following conditions, and have finally accomplished the present invention.

(1) It is effective at a low dose.

(2) It is effective against paddy field weeds and (or) against upland field weeds.

(3) It is also effective against perennial weeds and (or) hardly controllable weeds.

(4) It is effective in a wide range covering the germination stage to the growing stage.

(5) It has excellent residual effects and can be expected to provide stabilized effects.

(6) It is highly safe to crop plants.

Thus, the present invention provides a 9-phenylimino-8-thia-1,6-diazabicyclo[4.3.0]nonane-7-one derivative having the formula:

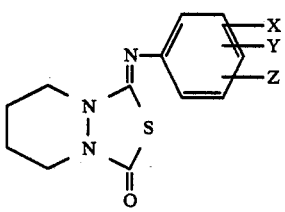 (I)

wherein each of X and Y is hydrogen or halogen such as chlorine, bromine, fluorine or iodine, and Z is

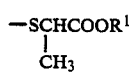

wherein $R^1$ is alkyl, preferably $C_1$–$C_6$ alkyl, or cycloalkyl, preferably $C_5$–$C_6$ cycloalkyl, or —$COOR^2$ wherein $R^2$ is alkyl, preferably $C_1$–$C_6$ alkyl.

Further, the present invention provides a herbicidal composition comprising a herbicidally effective amount of a compound of the formula I as defined above and a carrier.

DETAILED DESCRIPTION OF THE PREFERRED EMBODIMENTS

In the formula I, Z is preferably

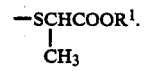

It is also preferred that X is hydrogen or halogen and Y is halogen.

A compound having the formula:

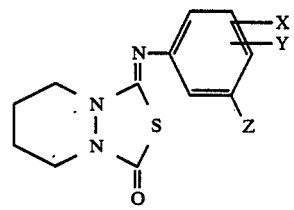

wherein X, Y and Z are as defined above, is particularly effective as a herbicide. Particularly preferred in this respect is a compound of the formula:

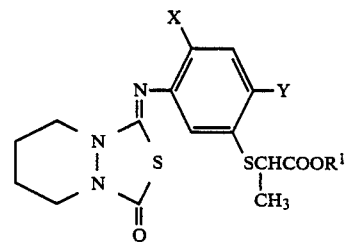

wherein X is hydrogen or halogen, particularly fluorine, Y is halogen, particularly chlorine, and $R^1$ is as defined above, particularly alkyl. Also preferred in this respect, is a compond having the formula:

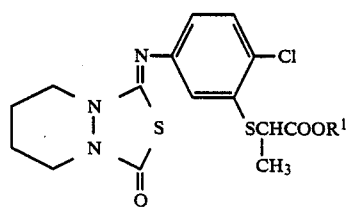

wherein $R^1$ is alkyl.

As a herbicide for a non-agricultural field, a compound of the formula:

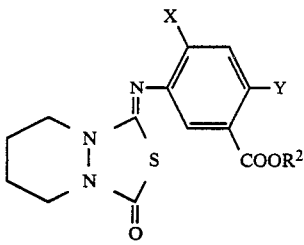

wherein each of X and Y is hydrogen, chlorine or fluorine, and $R^2$ is alkyl, is particularly useful. Particularly preferred in this respect is a compound wherein each of X and Y is chlorine or fluorine, or a compound wherein X is hydrogen and Y is chlorine.

Now, typical Examples of the compound of the formula I will be presented in Table 1. The compound Nos. indicated in the Table will be referred to in the subsequent description.

TABLE 1

| Compound No. | X, Y, Z substituents on phenyl ring | Physical property m. p. (°C.) or refractive index ($n_D^{20}$) |
|---|---|---|
| 1 | 4-Cl, 2-Cl, COOC₂H₅ | 81–83 |
| 2 | 4-F, 2-F, COOCH₃ | 112–114 |
| 3 | 4-F, 2-F, COOC₂H₅ | 91–92 |
| 4 | 4-F, 2-F, COOC₃H₇(n) | 67–69 |
| 5 | 4-F, 2-F, COOC₃H₇(i) | 86–88 |
| 6 | 2-Cl, SCH(CH₃)COOCH₃ | 1.6035 |
| 7 | 4-F, 2-Cl, SCH(CH₃)COOCH₃ | 1.6055 |
| 8 | 2-Cl, SCH(CH₃)COOC₃H₇(n) | 1.5955 |
| 9 | 4-F, 2-Cl, SCH(CH₃)COOC₃H₇(n) | 1.5929 |
| 10 | 2-Cl, SCH(CH₃)COOC₃H₇(i) | 1.5918 |
| 11 | 4-F, 2-Cl, SCH(CH₃)COOC₃H₇(i) | 1.5820 |
| 12 | 2-Cl, SCH(CH₃)COOC₄H₉(n) | 1.5922 |

TABLE 1-continued

| Compound No. | Structure | Physical property m.p. (°C.) or refractive index ($n_D^{20}$) |
|---|---|---|
| 13 | 4-F, 2-Cl-C6H3-SCH(CH3)COOC4H9(n) | 1.5749 |
| 14 | 2-Cl-C6H4-SCH(CH3)COOC4H9(sec) | 1.5861 |
| 15 | 2-Cl-C6H4-SCH(CH3)COOC4H9(sec) | 1.5755 |
| 16 | 2-Cl-C6H4-SCH(CH3)COOC4H9(i) | 1.5860 |
| 17 | 4-F, 2-Cl-C6H3-SCH(CH3)COOC4H9(i) | 1.5700 |
| 18 | 2-Cl-C6H4-SCH(CH3)COOC5H11(n) | 1.5820 |
| 19 | 4-F, 2-Cl-C6H3-SCH(CH3)COOC5H11(n) | 1.5760 |
| 20 | 2-Cl-C6H4-SCH(CH3)COO-cyclopentyl | 1.6071 |
| 21 | 4-F, 2-Cl-C6H3-SCH(CH3)COO-cyclohexyl | 1.5780 |

The compound of the formula I of the present invention can be prepared by the following process.

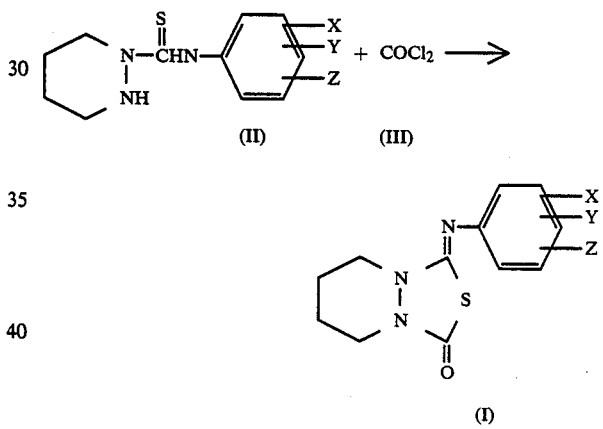

In the above formulas, X, Y and Z are as defined above. This process can be conducted by reacting the compound of the formula II with the compound of the formula III in the presence or absence of a base.

As the base, there may be mentioned an aliphatic tertiary amine such as triethylamine or trimethylamine; an aromatic tertiary amine such as pyridine, picoline or quinoline; or an inorganic base such as sodium hydroxide, potassium hydroxide, potassium carbonate or sodium carbonate.

The above reaction is preferably conducted in a solvent. As such a solvent, there may be mentioned a chlorine-containing hydrocarbon such as dichloromethane, chloroform or carbon tetrachloride; an ether such as diethyl ether, tetrahydrofuran or dioxane; a hydrocarbon such as n-hexane, benzene or toluene; an aliphatic ketone such as acetone or methyl ethyl ketone; dimethylsulfoxide; or N,N-dimethylformamide.

The above reaction can be completed in from 1 to 7 hours at a temperature within a range of from −20° C. to the boiling point of the solvent.

Now, the present invention will be described in further detail with reference to Examples. However, it should be understood that the present invention is by no means restricted by these specific Examples.

Firstly, Examples for the preparation of the compounds of the present invention will be described.

PREPARATION EXAMPLE 1

Preparation of 9-[4-chloro-3-(1-pentyloxycarbonylethylthio)-phenylimino]-8-thia-1,6-diazabicyclo[4.3.0]nonane-7-one (Compound No. 18)

Into a reaction flask, 1.6 g (3.7 mmol) of 1,2-tetramethylene-1-[4-chloro-3-(1-pentyloxycarbonylethylthio)phenylaminothiocarbonyl]hydrazine, 0.8 g (10 mmol) of pyridine and 20 ml of dichloromethane, were charged, and a dichloromethane solution containing 0.5 g (5 mmol) of phosgene was dropwise added while cooling the mixture with ice water. After the dropwise addition, the mixture was stirred at room temperature for 1 hour to complete the reaction. After the completion of the reaction, the reaction solution was washed with water and dried over anhydrous magnesium sulfate, and then the solvent was distilled off to obtain a crude product. This crude product was purified by silica gel column chromatography to obtain 1.1 g (yield: 65%) of colorless viscous substance. Refractive index $n_D^{20}$: 1.5820.

PREPARATION EXAMPLE 2

Preparation of 9-(2,4-difluoro-5-ethoxycarbonylphenylimino)-8-thia-1,6-diazabicyclo[4.3.0]nonane-7-thione (Compound No. 3)

Into a reaction flask, 4.0 g (12 mmol) of 1,2-tetramethylene-1-(2,4-difluoro-5-ethoxycarbonylphenylaminothiocarbonyl)hydrazine, 2.4 g (30 mmol) of pyridine and 20 ml of dichloromethane, were charged, and a dichloromethane solution containing 1.5 g (15 mmol) of phosgene was dropwise added while cooling the mixture with ice water. After the dropwise addition, the mixture was stirred at room temperature for 1 hour to complete the reaction. After the completion of the reaction, the reaction solution was washed with water and dried over anhydrous sodium sulfate, and then the solvent was distilled off to obtain a crude product. This crude product was purified by silica gel column chromatography to obtain 2.3 g (yield: 58%) of white crystals. Melting point: 91°–92° C.

PREPARATION EXAMPLE 3

Preparation of 9-(2,4-dichloro-5-ethoxycarbonylphenylimino)-8-thia-1,6-diazabicyclo[4.3.0]nonane-7-one (Compound No. 1)

Into a reaction flask, 2.7 g (25 mmol) of 1,2-tetramethylene-1-(2,4-dichloro-5-ethoxycarbonylphenylaminothiocarbonyl)hydrazine, 1.5 g (19 mmol) of pyridine and 20 ml of dichloromethane, were charged, and a dichloromethane solution containing 1.0 g of phosgene was dropwise added while cooling the mixture with ice water. After the dropwise addition, the mixture was stirred at room temperature for 1 hour to complete the reaction. After the completion of the reaction, the reaction solution was washed with water and dried over anhydrous sodium sulfate, and then the solvent was distilled off to obtain a crude product. This crude product was purified by silica gel column chromatography to obtain 1.7 g (yield: 59%) of white crystals. Melting point: 81°–83° C.

PREPARATION EXAMPLE 4

Preparation of 9-(2,4-difluoro-5-isopropoxycarbonylphenylimino)-8-thia-1,6-diazabicyclo[4.3.0]nonane-7-one (Compound No. 5)

Into a reaction flask, 3.0 g (8.7 mmol) of 1,2-tetramethylene-1-(2,4-difluoro-5-isopropoxycarbonylphenylaminothiocarbonyl)hydrazine, 1.7 g (22 mmol) of pyridine and 20 ml of dichloromethane, were charged, and a dichloromethane solution containing 1.1 g (11 mmol) of phosgene was dropwise added while cooling the mixture with ice water. After the dropwise addition the mixture was stirred at room temperature for 1 hour to complete the reaction. After the completion of the reaction, the reaction solution was washed with water and dried over anhydrous sodium sulfate, and then the solvent was distilled off to obtain a crude product. This crude product was purified by silica gel column chromatography to obtain 1.7 g (yield: 53%) of white crystals. Melting point: 86°–88° C.

The 9-phenylimino-8-thia-1,6-diazabicyclo[4.3.0]nonane-7-one derivative of the formula I is useful as an active ingredient for a herbicide. When the compound of the formula I of the present invention is used as a herbicide for a paddy rice field, an upland field, an orchard or a non-agricultural field, the active ingredient can be used in a suitable formulation depending upon the particular purpose. Usually, the active ingredient is diluted with an inert liquid or solid carrier, and used in the form of a formulation such as a dust, a wettable powder, an emulsifiable concentrate, a granule, etc., if necessary by adding a surfactant and other additives. Further, the compound of the present invention may be used in combination with an insecticide, a nematocide, a fungicide, other herbicides, a plant growth controlling agent, a fertilizer, etc., as the case requires.

Now, the formulations will be described in detail with reference to typical Formulation Examples. In the following Formulation Examples, "parts" means "parts by weight".

FORMULATION EXAMPLE 1

Wettable powder 10.0 parts of Compound No. 1, 0.5 part of Emulgen (trademark of Kao Corporation) 810, 0.5 part of Demol (trademark of Kao Corporation) N, 20.0 parts of Kunilite (trademark of Kunimine Industries Co., Ltd.) 201, and 69.0 parts of Zeeklite (trademark of Zeeklite Co., Ltd.) CA, were mixed and pulverized to obtain a wettable powder containing 10% of an active ingredient.

FORMULATION EXAMPLE 2

Wettable powder 10.0 parts of Compound No. 2, 0.5 part of Emulgen 810, 0.5 part of Demol N, 20.0 parts of Kunilite 201, 5.0 parts of Carplex 80 and 64.0 parts of Zeeklite CA, were mixed and pulverized to obtain a wettable powder containing 10% of the active ingredient.

FORMULATION EXAMPLE 3

Emulsifiable concentrate

To 30 parts of Compound No. 3, 60 parts of a mixture of xylene and isophorone in equal amounts and 10 parts of surfactant Sorpol (trademark of Toho Chemical Industry Co., Ltd.) 800A, were added, and the mixture was thoroughly mixed to obtain 100 parts of an emulsifiable concentrate.

FORMULATION EXAMPLE 4

Granules 10 parts of water was added to 10 parts of Compound No. 4, 80 parts of a filler obtained by mixing talc and bentonite in a ratio of 1:3, 5 parts of white carbon and 5 parts of surfactant Sorpol 800A, and the mixture was thoroughly kneaded to obtain a paste, which was extruded from sieve openings having a diameter of 0.7 mm and dried, and then cut into a length of from 0.5 to 1 mm, to obtain 100 parts of granules.

The compounds of the formula of the present invention exhibit excellent herbicidal effects at a very low dose in a wide range from the germination stage to the growing stage of annual weeds such as barnyardgrass (*Echinochloa crus-galli*), umbrella-plant (*Cyperus difformis* L.), monochoria (*Monochoria vaginalis* Presl), spike-flowered rotala (*Rotala indica* Koehne), false pimpernel (*Lindernia procumbens* Philcox) and *Dopatrium junceum* Hamilt, and perennial weeds such as bulrush (*Scirpus juncoides* Roxb.), slender spikerush (*Eleocharis acicularis* Roem, et Schult.), water-plantain (*Alisma canaliculatum* A. Br. et Bouche), sagittaria (*Sagittaria pygmaea* Miq.) and cyperus sp. (*Cyperus serotinus* Rottb.) which grow in paddy fields. At the same time, they have high selectivity for paddy field rice. Further, they exhibit high herbicidal effects, by soil treatment or by foliage treatment, against various weeds in the upland fields, for example, broad leaf weeds such as smart-weed (*Polygonum nodosum* L.), pigweed (*A,maranthus retroflexus*), lambsquaters (*Chenopodium album*), speed-well (*Veronica persica*), wild mustard (*Brassica kaber* var. *pinnatifida*), cocklebur (*Xanthium strumarium*), morning-glory (Ipomoea spp) and velvetleaf (*Abtilon theophrasti*), cyperaceous weeds such as rice flatsedge (*Cyperus iria* L.), and gramineous weeds such as barnyardgrass, large crabgrass (*Digitaria sanguinalis*) and green foxtail (*Setaria viridis*). At the same time, they have a feature that they are highly safe to crop plants such as upland rice, wheat, soybean and corn.

The dose of the compound of the present invention is usually within a range of from 1 g to 10 kg/ha. More specifically, the dose is usually from 5 to 5 kg/ha for upland fields, from 10 g to 1 kg/ha for paddy rice fields, and from 200 g to 5 kg/ha for non-agricultural fields.

Further, the compounds of the present invention have excellent residual effects, and show stabilized effects for a long period of time also in paddy fields. They are also useful for orchard, grassland, lawn and non-agricultural fields.

Now, the herbicidal effects of the herbicides of the present invention will be described with reference to Test Examples.

TEST EXAMPLE 1

Herbicidal test by soil treatment of paddy field

Into a porcelain pot having a diameter of 10 cm, paddy field soil was filled and puddled. Then, seeds of barnyardgrass, umbrella plant, monochoria and bulrush were sown, and water was introduced to a depth of 3 cm.

Next day, the wettable powder prepared in accordance with Formulation Example 1, was diluted with water and dropwise applied to the surface of the water. The amount of the active ingredient applied, was 400 g/10a. Then, the pot was left in a green house. Twenty one days after the application, the herbicidal effects were evaluated in accordance with the standards identified in Table 2. The results are shown in Tables 3 and 4.

TABLE 2

| Index | Herbicidal effects and phytotoxicity |
|---|---|
| 5 | Withered |
| 4.5 | Herbicidal effect (or phytotoxicity) in a range of 90 to 99% |
| 4 | Herbicidal effect (or phytotoxicity) in a range of 80 to 89% |
| 3.5 | Herbicidal effect (or phytotoxicity) in a range of 70 to 79% |
| 3 | Herbicidal effect (or phytotoxicity) in a range of 60 to 69% |
| 2.5 | Herbicidal effect (or phytotoxicity) in a range of 50 to 59% |
| 2 | Herbicidal effect (or phytotoxicity) in a range of 40 to 49% |
| 1.5 | Herbicidal effect (or phytotoxicity) in a range of 30 to 39% |
| 1 | Herbicidal effect (or phytotoxicity) in a range of 20 to 29% |
| 0.5 | Herbicidal effect (or phytotoxicity) in a range of 1 to 19% |
| 0 | No herbicidal effect (or no phytotoxicity) |

TABLE 3

| Compound No. | Herbicidal effects | | | |
|---|---|---|---|---|
| | Barnyard-grass | Umbrella plant | Monochoria | Bulrush |
| 1 | 5 | 5 | 5 | 5 |
| 2 | 5 | 5 | 5 | 5 |
| 3 | 5 | 5 | 5 | 5 |
| 4 | 5 | 5 | 5 | 5 |
| 5 | 5 | 5 | 5 | 5 |

TABLE 4

| Compound No. | Herbicidal effects | | | |
|---|---|---|---|---|
| | Barnyard-grass | Umbrella plant | Monochoria | Bulrush |
| 6 | 5 | 5 | 5 | 5 |
| 7 | 5 | 5 | 5 | 5 |
| 8 | 5 | 5 | 5 | 5 |
| 9 | 5 | 5 | 5 | 5 |
| 10 | 5 | 5 | 5 | 5 |
| 11 | 5 | 5 | 5 | 5 |
| 12 | 5 | 5 | 5 | 5 |
| 13 | 5 | 5 | 5 | 5 |
| 14 | 5 | 5 | 5 | 5 |
| 15 | 5 | 5 | 5 | 5 |
| 17 | 5 | 5 | 5 | 5 |
| 18 | 5 | 5 | 5 | 5 |
| 19 | 5 | 5 | 5 | 5 |
| 20 | 5 | 5 | 5 | 5 |
| 21 | 5 | 5 | 5 | 5 |

TEST EXAMPLE 2

The herbicidal test in soil treatment of upland field

Into a 120 cm$^2$ plastic pot, upland field soil was filled, and seeds of barnyardgrass, large crabgrass, smart-weed, pigweed and rice flatsedge were sown and covered with soil.

A wettable powder of each test compound formulated in accordance with Formulation Example 1, was diluted with water in an amount of 100 liter/10a and uniformly applied to the surface of soil by means of a small size spray at a dose of 400 g/10a of the active ingredient. After the application, the pot was left for 21 days in a green house, and then the herbicidal effects were evaluated in accordance with the standards identified in Table 2. The results are shown in Table 5.

TABLE 5

| Compound No. | Herbicidal effects | | | | |
|---|---|---|---|---|---|
| | Barnyard-grass | Large crabgrass | Smart-weed | Pigweed | Rice flatsedge |
| 1 | 5 | 5 | 5 | 5 | 5 |
| 5 | 4 | 5 | 5 | 5 | 5 |
| 6 | 5 | 5 | 5 | 5 | 5 |
| 7 | 5 | 5 | 5 | 5 | 5 |
| 9 | 5 | 5 | 5 | 5 | 5 |
| 10 | 4 | 5 | 5 | 5 | 5 |
| 13 | 5 | 5 | 5 | 5 | 5 |
| 14 | 5 | 5 | 4 | 5 | 5 |
| 15 | 5 | 5 | 5 | 5 | 5 |
| 21 | 5 | 5 | 5 | 5 | 5 |

TEST EXAMPLE 3

The herbicidal test in foliage treatment in upland field

Into a 120 cm² plastic pot, upland field soil was filled, and seeds of barnyardgrass, large crabgrass, smart weed, pigweed, lambsquaters and rice flatsedge, were sown, and grown in a green house until barnyardgrass grew to the 3 leaf stage. When barnyardgrass reached the 3 leaf stage, a wettable powder of each test compound formulated in accordance with Formulation Example 1 was diluted with water in an amount of 100 liter/10a and applied to the foliage of the plants from above by a small size spray at a dose of 400 g/10a of the active ingredient. After the application, the pot was left for 21 days in a green house, and then the herbicidal effects were evaluated in accordance with the standards identified in Table 2. The results are shown in Table 6.

TABLE 6

| Compound No. | Herbicidal effects | | | | | |
|---|---|---|---|---|---|---|
| | Barnyard-grass | Large crab-grass | Smart-weed | Pig-weed | Lambs-quarters | Rice flat-edge |
| 1 | 5 | 5 | 5 | 5 | 5 | 5 |
| 2 | 5 | 5 | 5 | 5 | 5 | 5 |
| 3 | 5 | 5 | 5 | 5 | 5 | 5 |
| 4 | 5 | 5 | 5 | 5 | 5 | 5 |
| 5 | 5 | 5 | 5 | 5 | 5 | 5 |
| 6 | 5 | 5 | 5 | 5 | 5 | 5 |
| 7 | 5 | 5 | 5 | 5 | 5 | 5 |
| 8 | 5 | 5 | 5 | 5 | 5 | 5 |
| 9 | 5 | 5 | 5 | 5 | 5 | 5 |
| 10 | 5 | 5 | 5 | 5 | 5 | 5 |
| 11 | 5 | 5 | 5 | 5 | 5 | 5 |
| 12 | 5 | 5 | 5 | 5 | 5 | 5 |
| 13 | 5 | 5 | 5 | 5 | 5 | 5 |
| 14 | 5 | 5 | 5 | 5 | 5 | 5 |
| 15 | 5 | 5 | 5 | 5 | 5 | 5 |
| 16 | 5 | 5 | 5 | 5 | 5 | 5 |
| 17 | 5 | 5 | 5 | 5 | 5 | 5 |
| 18 | 5 | 4 | 5 | 5 | 5 | 5 |
| 19 | 5 | 5 | 5 | 5 | 5 | 5 |
| 20 | 5 | 5 | 5 | 5 | 5 | 5 |
| 21 | 5 | 5 | 5 | 5 | 5 | 5 |

TEST EXAMPLE 4

The herbicidal and phytotoxicity tests in soil treatment of paddy field

Into 1/5,000a Wagner pot, paddy field soil was filled and puddled, and water was introduced thereto. In the pot, three germinated tubers of sagittaria were embended in the surface layer of the soil, and seeds of water plantain were sown in the surface layer of the soil. Further, two rice plants of 2.5 leaf stage were transplanted in a depth of 2 cm. Then, water was introduced to a depth of 3 cm. Next day, a prescribed amount of wettable powder formulated in accordance with Formulation Example 1, was diluted with water and dropwise applied to the water surface. Then, the pot was cultivated in a green house, and 30 days after the application, the herbicidal effect and phytotoxicity were evaluated in accordance with the standards identified in Table 2. The results are shown in Table 7.

TABLE 7

| Compound No. | Dose of active ingredients (g/10 a) | Herbicidal effects | | Phytotoxicity Transplanted paddy field rice |
|---|---|---|---|---|
| | | Water-plantain | Sagittaria | |
| 1 | 6.3 | 5 | 4 | 1.0 |
| 6 | 12.5 | 5 | 5 | 0 |
| 8 | 25 | 5 | 5 | 0 |
| 10 | 12.5 | 5 | 4 | 0 |
| 12 | 25 | 5 | 5 | 0 |
| 14 | 25 | 5 | 5 | 0 |
| 18 | 25 | 5 | 5 | 0 |
| 20 | 12.5 | 5 | 4 | 0.5 |
| Oxa-diazon | 50 | 5 | 5 | 2.0 |
| | 25 | 5 | 2 | 2.0 |
| | 12.5 | 5 | 1 | 1.0 |

TEST EXAMPLE 5

Selectivity test for soybean

Into a 330 cm² plastic pot, upland field soil was filled, and seeds of soybean, cocklebur, and morning-glory were sown. After cultivating in a green house for 14 days, a prescribed amount of a wettable powder formulated in accordance with Formulation Example 1 was diluted with water in an amount of 100 liter/10a and applied to the foliage of the plants from above by a small size spray. After the application, the pot was left in a green house for 21 days, and then the herbicidal effects and phytotoxicity were evaluated in accordance with the standards identified in Table 2. The results are shown in Table 8.

TABLE 8

| Compound No. | Dose of active ingredient (g/10a) | Herbicidal effect | | Phytotoxicity Soybean |
|---|---|---|---|---|
| | | Cocklebur | Morning-glory | |
| 6 | 1 | 4.5 | 4 | 0.5 |
| 8 | 3 | 5 | 5 | 1 |
| 9 | 1 | 5 | 4 | 0 |
| 11 | 3 | 5 | 5 | 0.5 |
| 13 | 3 | 5 | 4.5 | 0 |
| 14 | 3 | 5 | 4 | 0 |
| 15 | 3 | 5 | 4.5 | 0 |
| 16 | 10 | 5 | 4 | 0 |
| 17 | 1 | 4.5 | 4 | 0 |
| 18 | 3 | 4.5 | 5 | 0 |
| 19 | 3 | 5 | 5 | 0 |
| 21 | 3 | 5 | 4.5 | 0 |
| Oxadiazon | 50 | 3 | 2 | 1 |
| | 25 | 2 | 1 | 1 |
| | 6.3 | 0 | 0.5 | 0.5 |
| | 3 | 0 | 0 | 0 |

TEST EXAMPLE 6

Herbicidal and phytotoxicity test in the foliage treatment of upland field

Into a 330 cm² plastic pot, upland field soil was filled, and seeds of wheat, corn, pigweed, lambsquaters and velvetleaf were sown and grown in a green house until the corn grew to the 4 leaf stage. When the corn reached the 4 leaf stage, a prescribed amount of a wettable powder formulated in accordance with Formulation Example 1 was diluted with water in an amount of 100 liter/10a and applied to the foliage of the plants from above by a small size spray. After the application, the pot was left in a green house for 21 days, and then the herbicidal effects and phytotoxicity were evaluated in accordance with the standards identified in Table 2. The results a shown in Table 9.

TABLE 9

| Compound No. | Dose of active ingredient (g/10a) | Herbicidal effect | | | Phytotoxicity | |
|---|---|---|---|---|---|---|
| | | Pigweed | Lambsquaters | Velvet-Leaf | Wheat | Corn |
| 6 | 0.4 | 5 | 5 | 5 | 0.5 | 0 |
| 7 | 1.6 | 5 | 5 | 5 | 0 | 0 |
| 8 | 0.4 | 5 | 5 | 5 | 0 | 0 |
| 10 | 1.6 | 5 | 5 | 5 | 0.5 | 0 |
| 12 | 1.6 | 5 | 5 | 5 | 0.5 | 0.5 |
| 16 | 0.4 | 5 | 5 | 5 | 0 | 0.5 |
| 18 | 0.4 | 5 | 5 | 5 | 0 | 0 |
| 19 | 0.4 | 5 | 4.5 | 5 | 0 | 0 |
| 20 | 1.6 | 5 | 5 | 5 | 0 | 0.5 |
| 21 | 0.4 | 5 | 5 | 5 | 0 | 0 |
| Oxadiazone | 25 | 4.5 | 4.5 | 5 | 1.5 | 1.5 |
| | 6.3 | 2 | 3.5 | 4.5 | 1 | 1 |
| | 1.6 | 0.5 | 1 | 2.5 | 0 | 0 |

What is claimed is:

1. A 9-phenylimino-8-thia-1,6-diazabicyclo[4.3.0]nonane-7-one derivative having the formula:

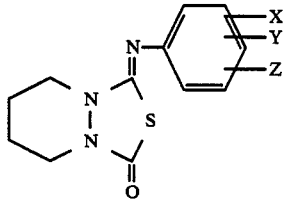

(I)

wherein each of X and Y is hydrogen or halogen, and Z is

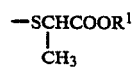

wherein $R^1$ is $C_1$-$C_6$ alkyl or $C_5$-$C_6$ cycloalkyl, or —COOR²
wherein $R^2$ is $C_1$-$C_6$ alkyl.

2. The compound according to claim 1, wherein Z is

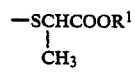

wherein $R^1$ is as defined in claim 1.

3. The compound according to claim 1, wherein $R^1$ is $C_1$-$C_6$ alkyl.

4. The compound according to claim 1, wherein $R^1$ is $C_5$-$C_6$ cycloalkyl.

5. The compound according to claim 1, wherein X is hydrogen or halogen and Y is halogen.

6. The compound according to claim 1, wherein X is hydrogen or halogen, Y is halogen, and Z is

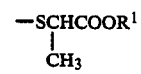

wherein $R^1$ is as defined in claim 1.

7. The compound according to claim 1, which has the formula:

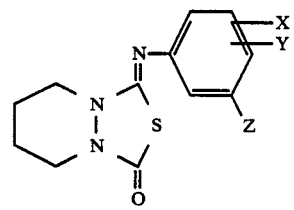

wherein X, Y and Z are as defined in claim 1.

8. The compound according to claim 1, which has the formula:

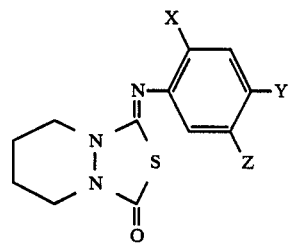

wherein X is hydrogen or halogen, Y is halogen, and Z is as defined in claim 1.

9. The compound according to claim 1, which has the formula:

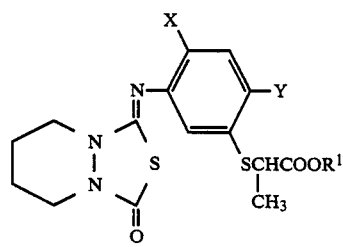

wherein X is hydrogen or halogen, Y is halogen, and $R^1$ is as defined in claim 1.

10. The compound according to claim 1, which has the formula:

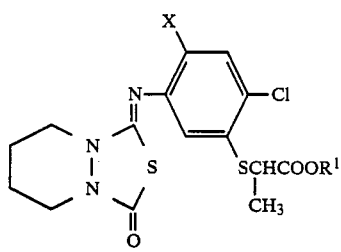

wherein X is hydrogen or fluorine, and $R^1$ is as defined in claim 1.

11. The compound according to claim 10, wherein $R^1$ is $C_1-C_6$ alkyl.

12. The compound according to claim 1, which has the formula:

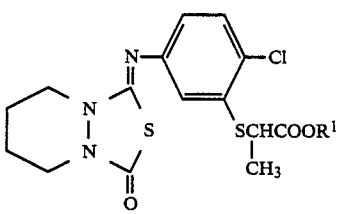

wherein $R^1$ is $C_1-C_6$ alkyl.

13. The compound according to claim 1, which has the formula:

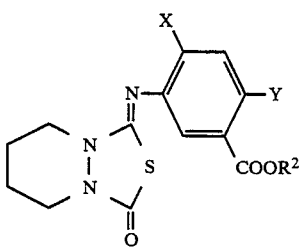

wherein each of X and Y is hydrogen, chlorine or fluorine, and $R^2$ is as defined in claim 1.

14. The compound according to claim 13, wherein each of X and Y is chlorine or fluorine.

15. The compound according to claim 1, of the formula:

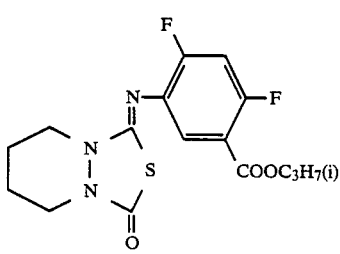

16. The compound according to claim 1, of the formula:

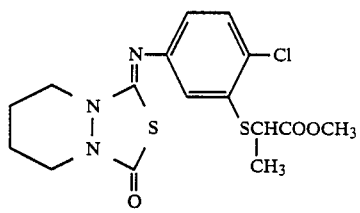

17. The compound according to claim 1, of the formula:

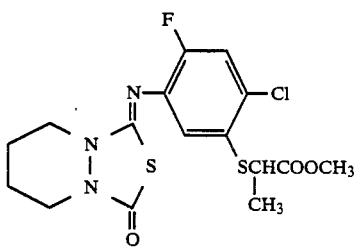

18. The compound according to claim 1, of the formula:

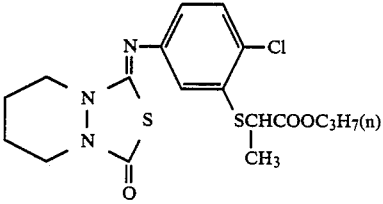

19. The compound according to claim 1, of the formula:

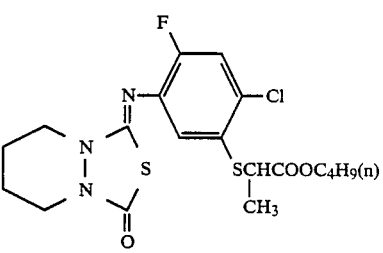

20. The compound according to claim 1, of the formula:

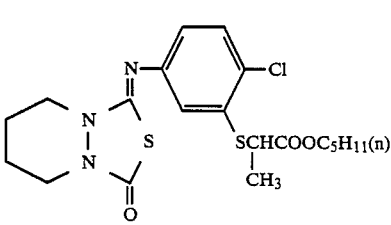

21. A herbicidal composition comprising a herbicidally effective amount of a compound of the formula I as defined in claim 1 and an agriculturally acceptable carrier.

* * * * *